US012369883B2

United States Patent
Bunn (10) Patent No.: US 12,369,883 B2
(45) Date of Patent: Jul. 29, 2025

(54) ARTIFICIAL INTELLIGENCE SYSTEM FOR DETERMINING CLINICAL VALUES THROUGH MEDICAL IMAGING

(71) Applicant: Ultrasound AI, Inc., Highlands Ranch, CO (US)

(72) Inventor: Robert S Bunn, Highlands Ranch, CO (US)

(73) Assignee: Ultrasound AI, Inc., Greenwood Village, CO (US)

( * ) Notice: Subject to any disclaimer, the term of this patent is extended or adjusted under 35 U.S.C. 154(b) by 0 days.

(21) Appl. No.: 18/431,566

(22) Filed: Feb. 2, 2024

(65) Prior Publication Data

US 2024/0173012 A1    May 30, 2024

Related U.S. Application Data (63) Continuation-in-part of application No. 17/573,246, filed on Jan. 11, 2022, now Pat. No. 11,969,289, (Continued)

(51) Int. Cl.
*A61B 8/00* (2006.01)
*A61B 8/06* (2006.01)
(Continued)

(52) U.S. Cl.
CPC .............. *A61B 8/0866* (2013.01); *A61B 8/06* (2013.01); *A61B 8/0875* (2013.01); (Continued)

(58) Field of Classification Search
CPC ....... A61B 8/0866; A61B 8/06; A61B 8/0875; A61B 8/0883; A61B 8/467; A61B 8/488; (Continued)

(56) References Cited

U.S. PATENT DOCUMENTS 8,828,981 B2   9/2014  Creasy et al.
10,650,929 B1 * 5/2020  Beck ...................... G06T 7/194
(Continued)

FOREIGN PATENT DOCUMENTS

IN    201941040741 A    4/2021
JP    2018-140172 A     9/2018
(Continued)

OTHER PUBLICATIONS

CN 202180043378.8, Response to first office action issued Dec. 28, 2023, dated May 10, 2024.
(Continued)

*Primary Examiner* — Joel F Brutus
(74) *Attorney, Agent, or Firm* — David J. Thibodeau, Jr.; VLP Law Group LLP (57) ABSTRACT

Systems and methods for establishing a patient's current or future clinical or lab values are provided. A neural network is trained on a dataset of medical images, such as ultrasound images, that are tagged with information concerning the lab values of people who were imaged to produce the medical images. The trained neural network can then be provided with medical images of a patient, and the neural network can then make a determination as to the patient's current or future clinical or lab values.

25 Claims, 2 Drawing Sheets

Related U.S. Application Data which is a continuation of application No. PCT/US2021/038164, filed on Jun. 20, 2021, and a continuation of application No. 17/352,290, filed on Jun. 19, 2021, now Pat. No. 11,266,376.

(60) Provisional application No. 63/443,169, filed on Feb. 3, 2023, provisional application No. 63/041,360, filed on Jun. 19, 2020.

(51) Int. Cl.
    *A61B 8/08*         (2006.01)
    *G06T 7/00*         (2017.01)
    *G06T 7/20*         (2017.01)
    *G16H 10/60*       (2018.01)
    *G16H 30/20*       (2018.01)
    *G16H 30/40*       (2018.01)
    *G16H 50/20*       (2018.01)

(52) U.S. Cl.
CPC ............ *A61B 8/0883* (2013.01); *A61B 8/467* (2013.01); *A61B 8/488* (2013.01); *G06T 7/0016* (2013.01); *G06T 7/20* (2013.01); *G16H 10/60* (2018.01); *G16H 30/20* (2018.01); *G16H 30/40* (2018.01); *G16H 50/20* (2018.01); *G06T 2207/10132* (2013.01); *G06T 2207/20081* (2013.01); *G06T 2207/30008* (2013.01); *G06T 2207/30044* (2013.01); *G06T 2207/30048* (2013.01); *G06T 2207/30104* (2013.01)

(58) Field of Classification Search
CPC . G06T 2207/10132; G06T 2207/20081; G06T 2207/30008; G06T 2207/30044; G06T 2207/30048; G06T 2207/30104
See application file for complete search history.

(56) References Cited

U.S. PATENT DOCUMENTS

| | | |
|---|---|---|
| 2004/0236193 A1 | 11/2004 | Sharf |
| 2006/0241510 A1 | 10/2006 | Halperin et al. |
| 2009/0093717 A1 | 4/2009 | Carneiro et al. |
| 2009/0169074 A1 | 7/2009 | Avinash et al. |
| 2010/0312115 A1 | 12/2010 | Dentinger |
| 2011/0248818 A1 | 10/2011 | Hashim-Waris |
| 2012/0135427 A1 | 5/2012 | Kypros et al. |
| 2014/0018678 A1 | 1/2014 | Donnelly et al. |
| 2014/0089004 A1 | 3/2014 | Frey et al. |
| 2015/0148657 A1 | 5/2015 | Shashar et al. |
| 2015/0342560 A1 | 12/2015 | Davey et al. |
| 2016/0071266 A1* | 3/2016 | Srivastava ............ G06T 7/0016 382/130 |
| 2016/0228505 A1 | 8/2016 | Stossel et al. |
| 2017/0000683 A1* | 1/2017 | Samec .................. A61B 5/369 |
| 2017/0086785 A1 | 3/2017 | Bjaerum |
| 2017/0091402 A1 | 3/2017 | Salafia et al. |
| 2017/0216335 A1 | 8/2017 | Mangano |
| 2017/0357844 A1 | 12/2017 | Comaniciu et al. |
| 2018/0032666 A1 | 2/2018 | Sun et al. |
| 2018/0153504 A1* | 6/2018 | Herickhoff ............ A61B 8/4472 |
| 2018/0247410 A1 | 8/2018 | Madabhushi et al. |
| 2019/0008674 A1 | 1/2019 | Myers et al. |
| 2019/0021698 A1 | 1/2019 | Raghavan et al. |
| 2019/0034590 A1 | 1/2019 | Oren et al. |
| 2019/0154704 A1 | 5/2019 | Davis et al. |
| 2019/0209116 A1 | 7/2019 | Sjöstrand et al. |
| 2019/0246904 A1 | 8/2019 | Kim et al. |
| 2019/0251638 A1 | 8/2019 | Braz et al. |
| 2019/0367987 A1 | 12/2019 | Hamamah et al. |
| 2020/0005899 A1 | 1/2020 | Nicula et al. |
| 2020/0005901 A1 | 1/2020 | Cohen et al. |
| 2020/0022674 A1 | 1/2020 | Egorov |
| 2020/0069292 A1* | 3/2020 | Abolmaesumi ...... A61B 8/5207 |
| 2020/0077947 A1 | 3/2020 | Shi et al. |
| 2020/0147006 A1 | 5/2020 | Charney et al. |
| 2020/0149110 A1 | 5/2020 | Targan et al. |
| 2020/0168310 A1 | 5/2020 | Westin et al. |
| 2020/0170614 A1 | 6/2020 | Kim et al. |
| 2021/0068905 A1 | 3/2021 | Quaid et al. |
| 2021/0090254 A1 | 3/2021 | Gong et al. |
| 2021/0118559 A1 | 4/2021 | Lefkofsky |
| 2021/0128115 A1 | 5/2021 | Mapiye et al. |
| 2021/0217166 A1 | 7/2021 | Graule et al. |
| 2021/0287513 A1 | 9/2021 | Mazar et al. |
| 2021/0307702 A1 | 10/2021 | Moon |
| 2022/0028551 A1 | 1/2022 | Jordan et al. |
| 2022/0067922 A1 | 3/2022 | Yu |
| 2022/0133260 A1 | 5/2022 | Bunn |
| 2022/0133280 A1 | 5/2022 | Urabe et al. |
| 2022/0164635 A1 | 5/2022 | Johansen et al. |
| 2022/0192501 A1 | 6/2022 | Shuler |
| 2022/0328189 A1 | 10/2022 | Zhou et al. |
| 2022/0400963 A1 | 12/2022 | Buckler et al. |

FOREIGN PATENT DOCUMENTS

| | | |
|---|---|---|
| KR | 10-2020-0013161 A | 2/2020 |
| WO | 2020/061590 A1 | 3/2020 |

OTHER PUBLICATIONS

CN 202180043378.8, Rejection Decision issued May 18, 2024.
CN 202180043378.8, Response to Rejection Decision iissued May 18, 2024, dated Aug. 19, 2024.
EP 21825348.2 EESR Issued Jun. 18, 2024.
Oelze et al., "Review of Quantitative Ultrasound: Envelope Statistics and Backscatter Coefficient Imaging and Contributions to Diagnostic Ultrasound", IEEE Transactions On Ultrasonics, Ferroelectrics, and Frequency Control, IEEE, USA, vol. 63, No. 2, Feb. 1, 2016 (Feb. 1, 2016), pp. 336-351, XP011597293, ISSN: 0885-3010, DOI: 10.1109/TUFFC.2015.2513958 [retrieved on Jan. 29, 2016].
Suff Natalie et al: "The prediction of preterm delivery: What is new?", Seminars in Fetal and Neonatal Medicine, Elsevier, GB, vol. 24, No. 1, Sep. 28, 2018 (Sep. 28, 2018), pp. 27-32, XP085591331, ISSN: 1744-165X, DOI: 10.1016/J.SINY.2018.09.006.
Pizzella Stephanie et al: "Evolving cervical imaging technologies to predict preterm birth", Seminars in Immunopathology, Springer Berlin Heidelberg, Berlin/Heidelberg, vol. 42, No. 4, Jun. 10, 2020 (Jun. 10, 2020), pp. 385-396, XP037251810, ISSN: 1863-2297, DOI: 10.1007/S00281-020-00800-5 [retrieved on Jun. 10, 2020].
Office Action Issued in related Chinese Patent Application No. 202180043378.8 issued Dec. 28, 2023, 27 pages.
PCT/US21/38164 International Search Report and Written Opinion, mailed Sep. 30, 2021.
PCT/US23/011845 International Search Report and Written Opinion, mailed Apr. 27, 2023.
PCT/US24/014349 International Search Report and Written Opinion, mailed May 7, 2024.
PCT/US24/019803 International Search Report and Written Opinion, mailed Jun. 17, 2024.
PCT/US24/014353 International Search Report and Written Opinion, mailed May 7, 2024.
PCT/US24/014356 International Search Report and Written Opinion, mailed May 9, 2024.
Kuo et al., "Automation of the kidney function prediction and classification through ultrasoundbased kidney imaging using deep learning." In: npj Digital Medicine vol. 2, Article No. 29 (2019), [onlinel [retrieved on Apr. 17, 2024 (Apr. 17, 2024)] Retrieved from the Internet < URL: https://www.nature.com/articles/s41746-019-0104-2#ethics>.
JP 2022-574786, Notice of Reasons for Refusal, Issued Sep. 3, 2024.
KR 10-2023-7000075, Office Action, Issued Oct. 21, 2024.

(56) References Cited

OTHER PUBLICATIONS

Response to Office Action dated Nov. 19, 2024 regarding Application No. JP2022-574786.
Response to Office Action dated Dec. 23, 2024 regarding Application No. KR10-2023-7000075.
Response to Office Action dated Dec. 30, 2024 regarding Application No. EP21825348.2.
Office Action dated Feb. 4, 2025 regarding Application No. JP2022-574786.
Kuo et al. "Automation of the kidney function prediction and classification through ultrasound-based kidney imaging using deep learning." In: npj Digital Medicine vol. 2, Article No. 29 (2019).
International Search Report and Written Opinion of PCTUS2021038164, dated Sep. 30, 2021.
International Search Report and Written Opinion of PCT/US2023/011845, dated Apr. 27, 2023.
International Search Report and Written Opinion of PCT/US2024/014349, dated May 7, 2024.
International Search Report and Written Opinion of PCT/US2024/019803, dated Jun. 17, 2024.
International Search Report and Written Opinion of PCT/US2024/014353, dated May 7, 2024.
International Search Report and Written Opinion of PCT/US2024/014356, dated May 9, 2024.

* cited by examiner

ARTIFICIAL INTELLIGENCE SYSTEM FOR DETERMINING CLINICAL VALUES THROUGH MEDICAL IMAGING

CROSS-REFERENCE TO RELATED APPLICATIONS

This application is a Continuation-In-Part of U.S. patent application Ser. No. 17/573,246 filed on Jan. 11, 2022 which is a Continuation of U.S. patent application Ser. No. 17/352,290 filed Jun. 19, 2021, now U.S. Pat. No. 11,266,376, which claims the benefit of U.S. Provisional Patent Application No. 63/041,360 filed on Jun. 19, 2020; U.S. patent application Ser. No. 17/573,246 also is a Continuation of International Application PCT/US21/38164 filed on Jun. 20, 2021. This application also claims the benefit of U.S. Provisional Patent Application No. 63/443,169 filed Feb. 3, 2023. The disclosures of each of the aforementioned patent applications are incorporated herein by reference.

BACKGROUND OF THE INVENTION

Field of the Invention

The invention pertains to the field of medical imaging and artificial intelligence, specifically focusing on using non-invasive medical imaging techniques and advanced machine learning algorithms to determine a patient's clinical or laboratory test values, promising to enhance laboratory testing speed and efficiency in healthcare and related sectors.

Description of the Prior Art

Traditional methods of clinical or laboratory value determination have primarily consisted of invasive blood or urine tests. These well-established techniques have been the standard for determining clinical or laboratory values within a patient. However, they come with inherent drawbacks such as invasiveness, time-consuming processes, and potential discomfort for patients. Furthermore, these methods do not provide real-time or continuous monitoring, which can limit their effectiveness in dynamic healthcare environments where timely interventions are critical.

SUMMARY

Ultrasound, and optionally other medical imaging techniques, are used to generate determinations regarding the specific clinical or laboratory values in a patient's system. These determinations involve identifying various and specific aspects of a patient's health based on the medical images. The determinations provide a novel method for determining and/or monitoring specific clinical values.

Various embodiments include using medical images, e.g., ultrasound images, as an input to a machine learning system configured to produce quantitative or qualitative determinations based on those images. These machine learning systems may use regression, a classification approach, and/or other machine learning algorithms. For example, any regression algorithm that outputs ranges may be used, e.g., quantile regression. In some embodiments, multiple algorithms are combined in a single AI in a unique approach.

Various embodiments also include preprocessing of images and/or pre-training of machine learning systems. For example, preprocessing of images has been found to be useful where medical images are of poor or variable quality or of variable size, e.g., where the images are ultrasound images.

Various embodiments of the invention comprise a medical diagnostic system configured to determine specific clinical values in a patient, the system comprising: an image storage configured to store medical images, the medical images including relevant anatomical structures or markers; image analysis logic configured to provide determinations of lab values based on the medical images; a user interface configured to provide at least the determinations of lab values to a user; and a microprocessor configured to execute at least a part of the image analysis logic. The image analysis logic optionally comprises logic configured to identify specific lab values in the patient's system based on the medical images.

Various embodiments of the invention include a method of generating quantitative or qualitative determinations of lab values. An exemplary method comprising: obtaining a set of medical images; analyzing the medical images using a machine learning system to produce quantitative determinations including the lab values for the patient; and providing the quantitative determinations to a user.

Various embodiments of the invention include a method of training a medical determination system, the method comprising: receiving a plurality of medical images; optionally filtering the images; optionally classifying the images according to the views or features included within the images; optionally pretraining a neural network to recognize features within the images or types of images; training the neural network to provide quantitative or qualitative determinations regarding lab values; and optionally testing the trained neural network to determine the accuracy of the quantitative or qualitative determinations.

Various embodiments of the invention include a method of acquiring medical images for training a neural network, the method comprising: creating a dataset of medical images; identifying relevant medical images in the dataset; and using the medical images to train a neural network to generate determinations of lab values from the medical images.

DETAILED DESCRIPTION

The systems and methods disclosed herein offer either quantitative or qualitative assessments of a patient's lab values. Here, a "quantitative determination" encompasses elements such as probability assessments, classifications into various lab value categories, or estimates of lab values. In the case of lab value estimation, it might be expressed, for example, as estimated milligrams per mL of urine. The advantage of quantitative determination lies in its capacity to provide considerably more actionable information compared to a mere qualitative classification.

Figure 1:
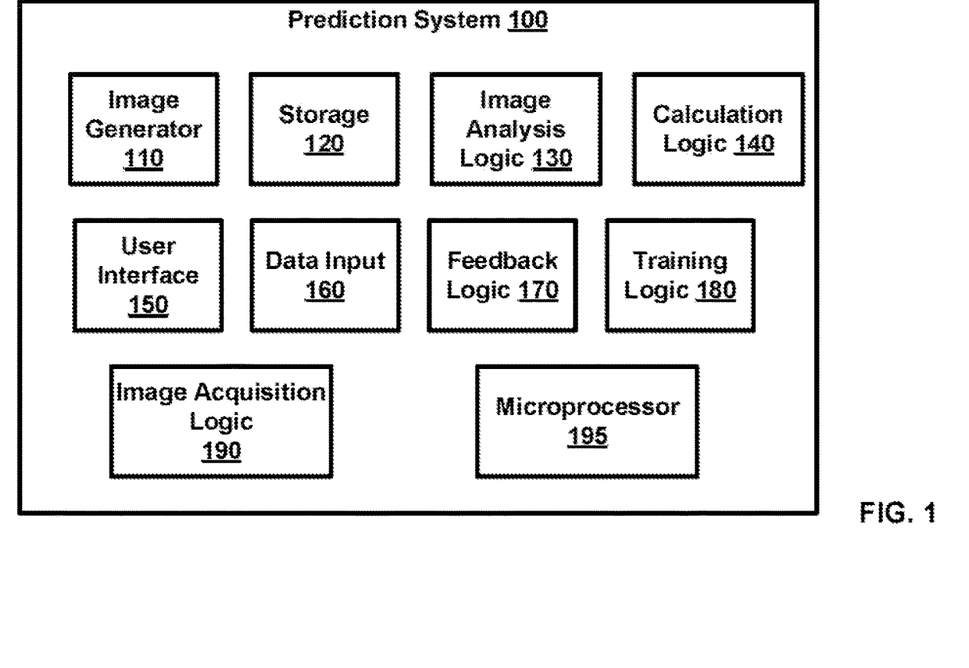
FIG. 1 illustrates medical diagnostic systems configured to determine a patient's lab value, according to various embodiments of the invention.

FIG. 1 depicts a medical Determination System 100, tailored for lab value determination, in accordance with various embodiments of the invention. Determination System 100 may comprise multiple devices, including an ultrasound system and a computing device geared towards image processing. Optionally, the components of the Determination System 100 communicate with each other and with external devices through a communication network like the Internet.

Image processing, aimed at generating determinations, encompasses the generation of estimates pertaining to the usage of specific lab values or classes of lab values. These estimates can be presented as absolute or relative probabilities.

Determination System 100 incorporates an optional Image Generator 110 responsible for producing medical images. Image Generator 110 may include a conventional ultrasound system or another imaging mechanism, configured to deliver images to other components within Determination System 100 for subsequent processing, such as via a computer network. In various embodiments, Image Generator 110 comprises a system that combines an image generation device with one or more elements of Determination System 100. For instance, Image Generator 110 can consist of an ultrasound device equipped with Storage 120, Image Analysis Logic 130, User Interface 150, and Feedback Logic 170, as discussed in greater detail elsewhere in this document. Image Generator 110 may also encompass diverse imaging technologies, such as radiographic (e.g., X-rays), magnetic resonance, nuclear, ultrasound, elastography, photoacoustic, tomography, echocardiography, magnetic particle imaging, spectroscopic (e.g., near-infrared), or similar devices and techniques. It should be noted that in this disclosure, references to ultrasound images are by way of example, and images from any of these other imaging techniques can be readily substituted for ultrasound images in these descriptions.

In some embodiments, various components of Determination System 100 are closely integrated with or housed within the Image Generator 110. To illustrate, consider Image Generator 110, which might encompass an ultrasound machine, housing Image Analysis Logic 130. This setup is adept at providing real-time feedback through Feedback Logic 170, effectively guiding the acquisition of ultrasound data and images.

In some embodiments, Image Generator 110 may involve a sound source, a sound detector, and accompanying logic, all orchestrated to generate ultrasound images based on the sounds detected by the sensor. Image Generator 110 is designed to adapt the generation of these ultrasound images based on feedback received from Image Analysis Logic 130. A practical example of this adaptability involves fine-tuning the sound generation, focus, and processing parameters to enhance the detection of blood perfusion in the minute lung capillaries. Such adjustments respond to cues from Image Analysis Logic 130, which might signal that images containing such information would yield more accurate determinations and estimates.

It's important to note that Image Generator 110 becomes an optional component in scenarios where externally acquired images are fed into Determination System 100, or in cases where raw imaging data forms the basis for determinations. For instance, in embodiments where raw ultrasound (sonogram) data is processed to generate medical assessments, Image Generator 110 may be excluded. In some configurations, images and/or raw data are relayed to Determination System 100 via a communication network, such as the Internet. The imagery produced by Image Generator 110 could encompass a sequence illustrating the dynamic movements of a beating heart. This sequence might reveal details like blood flow patterns, capillary perfusion, heartbeat rhythm, and more. It can even incorporate Doppler information, providing insights into the direction and velocity of these movements.

Determination System 100 also includes Storage 120. This component contains digital memory capabilities for storing an array of data types. Its storage capacity can accommodate raw sensor data, medical images, medical records, executable code (logic), neural networks, and other related data. For instance, it can house raw sensor data captured by a photon or acoustic detector, a dataset instrumental in generating images like X-rays or ultrasound scans. Storage 120, as discussed throughout this document, comprises memory circuits and data structures designed to manage and store the mentioned data categories. When dealing with ultrasound images, these images may optionally be configured at 600×600 pixels, optionally encompassing randomly selected crops of 400×400 pixels, which can be used in the training and determinations outlined herein. The term "ultrasound images" in this context may also encompass three-dimensional renderings created from ultrasound data.

In certain embodiments, Storage 120 is designed with circuits for the storage of ultrasound images acquired from patients. These ultrasound images can be collected in one or more separate acquisition sessions. For instance, during the first session, a sonographer might gather an initial set of ultrasound images, and subsequently, a second set of images may be procured in a subsequent session taking place at intervals of at least 1, 2, 5, 7, 15, 21, 30, 60, 90, or 365 days, or within any range between these durations. The ultrasound images for a particular patient may span over a duration encompassing any of the mentioned timeframes. In some instances, a patient could undergo weekly ultrasound sessions. These ultrasound images may encompass Doppler data and even sequences of images (e.g., videos) illustrating the motion of various anatomical structures. Examples include images that reveal heartbeats or blood flow, and they may also incorporate data pertaining to the density of tissues, fluids, or bone. Images deemed valuable for making lab value determinations encompass a broad spectrum, such as those depicting heart rate, liver condition, uterine status, intestinal health, femur and humerus structure, endometrial features (e.g., thickness and vascularization), kidney function, placental status, adnexa assessment, and so forth.

Determination System 100 further contains Image Analysis Logic 130. It is useful in providing either quantitative or qualitative determinations regarding a patient's lab values, derived from the ultrasound images and optionally supplemented by clinical data. These determinations come in various formats. For instance, these determinations might incorporate estimates that encompass a wide array of patient-specific factors, such as potential co-morbidities.

In some embodiments, Image Analysis Logic 130 comprises two distinct logic components. The first logic is designed to ascertain a specific lab value based on the ultrasound images, while the second logic is tasked with determining if that lab value will likely change within some specific time frame based on the same set of ultrasound images. For example, the first logic could analyze ultrasound images to determine a lab value at the time the images were generated, while the second logic focuses on determining the future state of a lab value. Both the first and second logic components can be housed within the same machine learning system for cohesive analysis.

Image Analysis Logic 130 exhibits adaptability when selecting machine learning algorithms for its calculations.

For instance, in some embodiments, Image Analysis Logic 130 is configured to employ a regression algorithm, such as quantile regression, to furnish determinations about lab values and optionally even estimate expected changes in lab values in the future. These regression methods predict a range within which the actual answer is likely to fall, as opposed to a single point value. Any regression system capable of predicting ranges rather than specific values may be employed in Image Analysis Logic 130. This use of a range-based estimation helps to prevent overfitting of the data and proves valuable when the ultrasound images used for training may have mislabeled attributes. Image Analysis Logic 130 typically bases determinations and estimates on sets of ultrasound images, rather than relying on the analysis of a single ultrasound image.

In alternative embodiments, Image Analysis Logic 130 is programmed to determine lab values utilizing classification algorithms. These classifications can include categories such as "Low," "Normal," or "High," among others. When classification algorithms are deployed, a "label smoothing" function may be applied. This smoothing function is particularly useful because certain training images may contain incorrect labels due to human error at the time of ultrasound image generation. The smoothing function may take a specific form, possibly involving epsilon ($\varepsilon$) values of 0.05, 0.1, 0.3, or even greater.

Sample Label Smoothing

Instead of using one-hot encoded vector, a noise distribution $u(y|x)$ is introduced. The new ground truth label for data $(x_i, y_i)$ becomes:

$$p'(y \mid x_i) = (1 - \varepsilon)p(y \mid x_i) + \varepsilon u(y \mid x_i)$$

$$= \begin{cases} 1 - \varepsilon + \varepsilon u(y \mid x_i) & \text{if } y = y_i \\ \varepsilon u(y \mid x_i) & \text{otherwise} \end{cases}$$

Where $\varepsilon$ is a weight factor, $\varepsilon \in [0, 1]$, and note that $\sum_{y=1}^{K} p'(y|x_i) = 1$ This new ground truth label is used as a replacement for the one-hot encoded ground-truth label in a loss function.

$$L' = -\sum_{i=1}^{n} \sum_{y=1}^{K} p'(y \mid x_i) \log q_\theta(y \mid x_i)$$

$$= -\sum_{i=1}^{n} \sum_{y=1}^{K} [(1 - \varepsilon)p(y \mid x_i) + \varepsilon u(y \mid x_i)] \log q_\theta(y \mid x_i)$$

Or, $$L' = \sum_{i=1}^{n} \left\{ (1 - \varepsilon) \left[ -\sum_{y=1}^{K} p(y \mid x_i) \log q_\theta(y \mid x_i) \right] + \varepsilon \left[ -\sum_{y=1}^{K} u(y \mid x_i) \log q_\theta(y \mid x_i) \right] \right\}$$

$$= \sum_{i=1}^{n} [(1 - \varepsilon) H_i(p, q_\theta) + \varepsilon H_i(u, q_\theta)]$$

One can see that for each example in the training dataset, the loss contribution is a mixture of the cross entropy between the one-hot encoded distribution and the predicted distribution $H_i(p, q_\theta)$, and the cross entropy between the noise distribution and the predicted distribution ($H_i(u, q_\theta)$. During training, if the model learns to predict the distribution confidently, $H_i(\overline{p}, q_\theta)$ will go close to zero, but $H_i(u, q_\theta)$ will increase dramatically. Therefore, with label smoothing, one introduces a regularizer $H_i(u, q_\theta)$ to prevent the model from predicting too confidently.

In some embodiments, label smoothing is used when the loss function is cross entropy, and the model applies the softmax function to the penultimate layer's logit vectors z to compute its output probabilities p. Label smoothing is a regularization technique for classification problems to prevent the model from predicting the labels too confidently during training and generalizing poorly. See, for example, https://leimao.github.io/blog/Label-Smoothing/.

In some embodiments, both a regression algorithm and a classification algorithm are used to determine lab values and/or future lab values. For example, Image Analysis Logic 130 can include two separate neural networks, one configured to apply the regression algorithm (that outputs a range) and the other configured to apply the classification algorithm. In this case, the classification algorithm may be applied before the regression algorithm and the regression algorithm is optionally applied separately to each class.

Alternatively, both the regression algorithm and the classification algorithm may be applied by the same neural network. In such embodiments, the neural network is trained to produce both a classification and a regression-based prediction, both of which are quantitative. A regression algorithm outputs one or more values for each percentile chosen. For example, some embodiments use 10%, 25%, 50%, 75%, 90% percentiles for outputs (which represent percentiles of a quantitative prediction), and each of these percentiles may be associated with a probability and/or a confidence measure. From a set of image inputs, the neural network of Image Analysis Logic 130 typically generates one or more values for each percentile chosen. Multiple outputs from distinct algorithms may be used to confirm a determination of current lab values and/or future lab values. This scenario is optionally used to establish confidence in the overall prediction since the regression and classification algorithms should produce the same result.

Image Analysis Logic 130 may employ other machine learning algorithms or combinations thereof, in addition to or as an alternative to regression and classification. For example, Image Analysis Logic 130 may be configured to apply a regression that outputs an estimated range, a range being more accurate and/or useful than single point predictions. However, single point predictions can be used if many neural networks are generated (each trained on a different subset of the images/data) from different subsets of the data, which are then statistically analyzed to form an average and/or distribution. In some embodiments, a Bayesian neural network is used to capture the epistemic uncertainty, which is the uncertainty about the model fitness due to limited training data. Specifically, instead of learning specific weight (and bias) values in the neural network, the Bayesian approach learns weight distributions, from which it samples to produce an output for a given input, to encode weight uncertainty. Bayesian networks can also be used in a similar fashion in the classification approaches to prediction discussed herein.

As previously highlighted, Image Analysis Logic 130 can be configured, employing the aforementioned algorithmic and machine learning techniques, to discern a problem with a current lab value or a problem with a future lab value. This determination extends to encompass a multitude of facets, including the likelihood of a future abnormal lab value, and the current lab value. These assessments are grounded in the comprehensive analysis of ultrasound images, potentially complemented by additional patient-related factors. For instance, Image Analysis Logic 130 may be tailored to derive the aforementioned evaluations from clinical data. This clinical dataset might encompass a range of variables, such as genetics, body weight, patient medical history, blood glucose levels, heart functionality, kidney performance, blood pressure readings, infection status, nutritional profiles, substance use (including smoking and alcohol consumption habits), patient age, socioeconomic status, living environment, income levels, and even ancestral background. Image Analysis Logic 130 can be strategically configured to accept any singular element from this clinical dataset or combine multiple factors to generate the estimates and determinations discussed herein, partly predicated on this clinical information.

Optionally, Determination System 100 integrates Calculation Logic 140, designed to derive outputs based on the estimates generated by Image Analysis Logic 130. For instance, Calculation Logic 140 can be programmed to compute a current lab value, alongside an estimate of a future lab value. Calculation Logic 140 may achieve this by calculating a lab value through the utilization of a probability distribution, represented, for instance, in percentiles. Furthermore, Calculation Logic 140 can ascertain the probability of an abnormal lab value by employing a distribution function on the estimates provided by Image Analysis Logic 130 and subsequently generating a probability distribution based on this data. In certain embodiments, Image Analysis Logic 130 is equipped to generate specific characteristics associated with this distribution function. For example, in select instances, an estimation of lab value determination reliability can be factored into the determination, allowing for the calculation of a width parameter (e.g., standard deviation) of the distribution function. It's important to note that Calculation Logic 140 may be integrated within Image Analysis Logic 110, offering an alternative approach to processing and analysis.

Determination System 100 optionally further includes a User Interface 150 configured to provide to a user estimates and/or determinations made using Image Analysis Logic 130. User Interface 150 optionally includes a graphical user interface (and the logic associated therewith) and may be displayed on an instance of Image Generator 110, a mobile device (in which case User Interface 150 can include a mobile app.) or on a computing device remote from Image Generator 110 and/or Image Analysis Logic 130. For example, User Interface 150 may be configured to display at least one or two of: current lab values, and future lab values. In some embodiments, User Interface 150 is configured for a remote user to upload one or more ultrasound images for processing by Image Analysis Logic 130.

As is discussed further herein, in some embodiments, User Interface 150 is configured to provide feedback to a user in real-time. For example, User Interface 150 may be used to give instructions to an ultrasound technician during an ultrasound session, to generate images which result in a better determination and/or an estimate related to current and future lab values.

Determination System 100 optionally further includes a Data Input 160 configured to receive data regarding a patient, e.g., clinical data regarding the patient. Data Input 160 is optionally configured to receive any of the clinical data discussed herein, which may be used by Image Analysis Logic 130 to generate the estimates and/or probabilities discussed herein. For example, this data can include any of the clinical data discussed herein, or inputs from a user of Image Generator 110. In some embodiments, Data Input 160 is configured to receive medical images, such as ultrasound images, from remote sources.

Determination System 100 optionally further includes Feedback Logic 170. Feedback Logic 170 is configured to guide acquisition of ultrasound images based on a quality of the estimate and/or determinations related to the patient. For example, if analysis of ultrasound images, using Image Analysis Logic 130, obtained during an imaging session, results in determinations and/or estimates having inadequate precision, accuracy, and/or reliability, then Feedback Logic 170 may use User Interface 150 to inform a user that additional ultrasound images are desirable.

Further, in some embodiments, feedback logic is configured to direct a user to obtain ultrasound images of specific features such as motion of a heartbeat, heart rate, the liver, the kidneys, blood flow, bone development, spine, capillary perfusion, uterus, ovaries, testicles, femur, humerus, endometrium, endometrium vascularization, the adnexa, and/or the like. In some embodiments, Image Analysis Logic 130 is configured to classify ultrasound images according to subject matter and/or objects included within the images. For example, separate subject matter classes may include any of the views and/or features discussed herein. In such embodiments, Image Analysis Logic 130 may be configured to identify objects in the ultrasound images and determine that there are sufficient quality images of objects in each subject matter classification. (Subject matter classification is not to be confused with classification of ultrasound images according to lab value determination.) If there are not sufficient images, then the User Interface 150 may be used to request that the operator of Image Generator 110 obtain additional images including the additional objects. Feedback Logic 170, thus, may be configured to indicate a need to acquire additional ultrasound images useful in the estimation that the patient is currently using a pharmaceutical. In a specific example, Image Analysis Logic 130 may be configured to request at least one set of images indicative of a current lab value and at least one set of images indicative of a future lab value. In some instances, Feedback Logic 270 is configured to guide the positioning of the image generator (e.g., an ultrasound head) so as to generate images that are more useful in the estimation of a current or future lab value. Such guidance may include positioning of an ultrasound probe in a specific position or a written/audio request such as "obtain images showing entire bladder."

In various embodiments, Feedback Logic 170 is configured to guide or request acquisition of new images that would be beneficial to training future models to obtain greater accuracy.

Determination System 100 optionally further includes Training Logic 180. Training Logic 180 is configured for training Image Analysis Logic 130, Feedback Logic 170, Image Acquisition Logic 190, and/or any other machine learning system discussed herein. Such training is typically directed at the end goal of learning to make quantitative determinations and/or estimates relating to a patient's current or future lab values. For example, Training Logic 180 may be configured to train Image Analysis Logic 130 to make a quantitative determination and/or estimate of a lab value. As described elsewhere herein, this determination may be made using both a quantile regression algorithm and a classification algorithm, together or separately.

While Training Logic 180 may use any applicable selections of the commonly known neural network training algorithms, Training Logic 180 optionally includes a variety of improvements to better train the neural networks disclosed herein. For example, in some embodiments Training Logic 180 is configured to pretrain a neural network of Image Analysis Logic 130 to better recognize features in ultrasound images. This pretraining can include training on images with varying orientation, contrast, resolution, point of view, etc., and can be directed at recognizing anatomical features within the ultrasound images. Pretraining is optionally performed using unlabeled data.

In some embodiments, Training Logic 180 is configured to generate additional training images, in cases where training images for a specific condition are sparse or infrequent. For example, once it is known which images and features are most predictive, Training Logic 180 can take subsets of the images, and use a GAN (Generative Adversarial Network) to generate new training images including the features that predict rare lab values.

In some embodiments, Training Logic 180 is configured to train on multiple sets of images, the images optionally being from different patients. By training on multiple sets of images, rather than on single images, overfitting of the data can be reduced. Preferably, each of the sets is large enough to assure that there are at least some images within the set including information useful for making the quantitative determinations discussed herein.

In some embodiments, Training Logic 180 is configured to train Image Analysis Logic 130 to enhance images. For example, Image Analysis Logic 130 may be pretrained to enhance poor quality ultrasound images, or to reveal features, such as capillary perfusion and/or vascularization, that would not normally be visible in the ultrasound images being processed. Such enhancement may allow the use of a handheld ultrasound image to generate the images processed to make quantitative determinations related to current or future lab values.

In some embodiments, Training Logic 180 is configured to train neural networks in multiple stages, e.g., as in transfer learning. For example, a neural network may first be trained to recognize relevant patient features, and then be trained to estimate current or future lab values.

Determination System 100 typically further includes a Microprocessor 195 configured to execute some or all of the logic described herein. For example, Microprocessor 195 may be configured to execute parts of Image Analysis Logic 130, Calculation Logic 140, Feedback Logic 170, Training Logic 180, and/or Image Acquisition Logic 190. Microprocessor 195 may include circuits and/or optical components configured to perform these functions.

Figure 2:
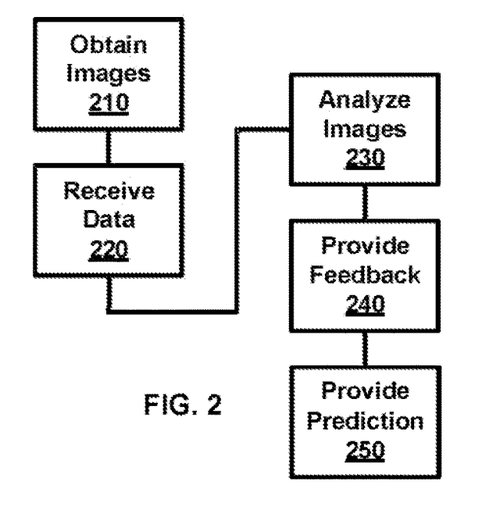
FIG. 2 illustrates methods of making a quantitative determination according to various embodiments of the invention.

FIG. 2 illustrates methods of making a quantitative (optionally medical) determination, according to various embodiments of the invention.

In an Obtain Images Step 210, a set of one or more images are obtained. These images are typically related to a specific patient. These images may be obtained from a source external to Determination System 100 or may be obtained using Image Generator 110. For example, in some embodiments, ultrasound images are uploaded to Storage 120 via a computer network such as the internet. Images may be received from an electronic medical records system. In other embodiments, images are generated using a medical imaging system such as any of those discussed herein. The images are optionally stored in Storage 120. The images can include any combination of the views and/or features discussed herein and are optionally classified based on their respective views and features (subject matter classification).

In an optional Receive Data Step 220, additional clinical data regarding the patient is received. Again, this data may be received from an electronic medical records system, provided by the patient, and/or provided by a caregiver. The received clinical data can include any of the clinical data discussed herein and is optionally received via Data Input 160.

In an Analyze Images Step 230 the images obtained in Obtain Images Step 210 are analyzed using Image Analysis Logic 130. The images are analyzed to produce one or more quantitative or qualitative determinations. For example, a quantitative determination can include an estimate of a current lab value, or an estimate of a future lab value. The determination is a "quantitative determination" as defined elsewhere herein. In addition to the images, the quantitative determination is optionally further based on the clinical data received in Receive Data Step 220. The methods of analysis in Analyze Images Step 230 can include any combination of the algorithms and/or machine learning systems discussed elsewhere herein, including those discussed with reference to Image Analysis Logic 130. For example, analyzing medical images can include using a quantile regression algorithm and/or a classification algorithm to make a quantitative determination relating to a current or a future lab value. In another example, analyzing the medical images includes using a regression algorithm to provide an estimate of a current or future lab value, the regression algorithm being configured to determine an estimated time of a future lab value into one or multiple time ranges.

In an optional Provide Feedback Step 240, a user (e.g., a caregiver, or possibly the patient) is provided with feedback regarding acquisition of the images. This feedback can be based on, for example, a quality of the quantitative determination and/or a classification of images already acquired. In specific examples, during an ultrasound session, a caregiver may be asked to acquire additional images of different resolution, of different views, of different features, and/or the like. Obtain Images Step 210 and Analyze Images Step 230 are optionally repeated following Provide Feedback Step 240.

In a Provide Determination Step 250 the quantitative or qualitative determination(s) generated in Analyze Images Step 230 is provided to a user, e.g., a patient or caregiver. The determinations are optionally also placed in Storage 120 and/or an electronic medical records (EMR) system. In various embodiments, the determinations are provided via a web interface, via the EMR system, via a mobile application, on a display of Image Generator 110, on a display of a computing device, and/or the like.

Figure 3:
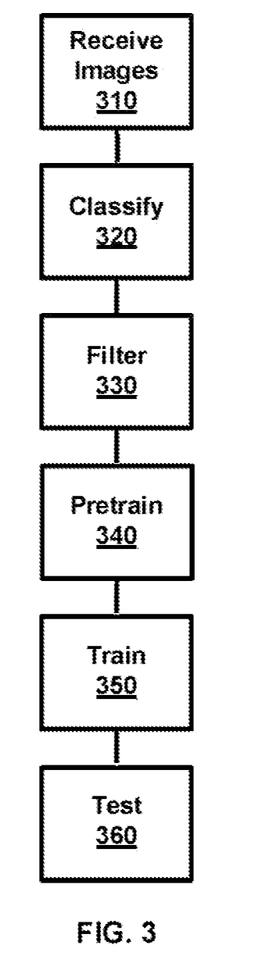
FIG. 3 illustrates methods of training a medical diagnostic system according to various embodiments of the invention.

FIG. 3 illustrates methods of training a medical determination system, according to various embodiments of the invention. The methods illustrated by FIG. 3 are optionally used to train Image Analysis Logic 130, Feedback Logic 170, and/or Image Acquisition Logic 190. The methods may be performed using Training Logic 180.

In a Receive Images Step 310, a plurality of medical images are received as a training set. The received medical images optionally include ultrasound images of a patient with multiple lab values to provide a means of calibration for an individual patient. The received images are optionally stored in Storage 120.

In an optional Classify Step 320, the received images are classified according to the views or features included within the images. For example, an image may be classified as showing the kidney or classified as showing the liver. Classify Step 320 is optionally performed by a neural network included in Image Analysis Logic 130 and/or trained by Training Logic 180. Classify Step 320 may also include classifying images according to current or future lab values. For example, images may be classified as having been generated at a specific current or future lab value. It should be noted that as used herein, "neural network" specifically excludes human brains.

In an optional Filter Step 330, the received images are filtered. Filtering can include removing images that lack features or views that have been determined to have little or no determinative value. For example, a class of images of a bladder may be determined to have little value in determining a quantitative or qualitative determination, and this class of images may be removed from the training set. Images may also be filtered according to their quality or resolution, etc.

In some embodiments, Filter Step 330 includes balancing of a number of images in various classes. For example, for training purposes, it may be desirable to have roughly equal numbers of rare lab values. Specifically, balancing may be used to adjust quantities of the images based on the lab value. Likewise, for training purposes, it may be desirable to balance numbers of images within the training set based on classification of views and/or features as determined in Classify Step 320.

In an optional Pretrain Step 340, the neural network is optionally pretrained to recognize features within the images or types of images. For example, a neural network within Image Analysis Logic 130 may be pretrained to recognize features in ultrasound images of varying orientation, resolution, and/or quality.

In a Train Step 350, the neural network is trained to provide a quantitative or qualitative determination regarding current or future lab values. As discussed elsewhere herein, the quantitative determination can include an estimate of a current or future lab value.

In an optional Test Step 360, determinations made by the neural network trained in Train Step 350 are tested using test images. This testing may be performed to determine the accuracy and/or precision of the quantitative or qualitative determinations generated by the neural network.

The quantitative or qualitative determination of a current or future lab value is optionally used to selectively select a population for a clinical trial. For example, assuming that a predicted future lab value occurs in less than 1% of patients, it would be inefficient to give a general population of patients a candidate therapy in order to detect a benefit to the unidentified 1% of patients. However, by identifying the 1% of the patients most likely to have a specific future lab value a study can be made of the benefit seen within this population for a candidate therapy. Such a study is much more efficient and more likely to reveal benefits with better statistical relevance. The systems and methods disclosed herein may be used to identify such preferred populations for clinical studies. This approach is particularly beneficial for conditions that begin development (and could benefit from therapy) well before clear symptoms appear, e.g., high blood pressure.

The various methods illustrated in FIGS. 2 and 3 are optionally used in combination and are optionally performed using the systems illustrated by FIG. 1. For example, the methods of FIGS. 2 and 3 may be used together.

It should be understood that the present invention is not limited to only known lab values, methods described herein can be used for identifying new lab values that could not easily be determined in some other manner. In addition to determining current and future lab values, the present invention can also be utilized to create lab values that could measure things such as rate and/or acceleration of degradation of a physiological function or organ. Those of ordinary skill will be able to identify still other conditions that AI can be trained to determine. This invention can also be used to calibrate an optimum lab value for an individual patient as well as a means of calibrating the determinations based on the uniqueness of individuals. These steps may also be used to determine optimal lab values for specific patients due to conditions that may need a lab value not typically regarded as normal.

EXAMPLE

The following is an illustrative example, which may be included in any of the embodiments discussed herein:

All ultrasounds from any patient are used to train the neural networks discussed herein. However, different models can be created for different lab values or classes of lab values.

Note: The following models are simply individual embodiments that show how to create a working model. Many of the hyperparameters such as the learning rate, batch size, and number of epochs can be adjusted without issue.

A machine learning algorithm (the code), set forth below, was created and used to train a neural network to make determinations whether a patient currently has high blood pressure, based on ultrasound images acquired from the patient. Both transformer and CNN architectures were successfully used. The images were acquired of various anatomical areas. The dataset was split into a training set and a validation set. Ten percent of patients were selected randomly to comprise the validation set, the remaining images comprised the training set. Next, using the labeled data in the training set, the algorithm gradually learned to extract relevant features from these images, such as anatomical structures that may be different depending on high blood pressure, but not necessarily visible to the human eye. During the training session the algorithm was repeatedly tested against the validation set which does not participate in the training. The algorithm's performance was evaluated on the validation set of ultrasound images that had not been used for training, and the algorithm's predictions were compared against the actual labels. The training was halted once the validation accuracy began to decrease after reaching a peak accuracy, indicating the algorithm was likely no longer learning generalized features, but more likely memorizing features of the training set. The algorithm proved accurate on the validation data, yielding an accuracy of 79%, and was therefore ready to be deployed for use on images of anatomy that are affected in some physiological way by high blood pressure and not part of the initial training dataset.

Import all the libraries used in the code from fastai.vision.all import*

Any imaging study where the patient was determined to have high blood pressure at the time of the imaging study can be labeled "Hypertension", or "Normal" if patient did not have high blood pressure at time of the imaging study. However, this labeling is not strictly necessary; other classification labels may be used.

The following path is a folder containing one subfolder for each class to be predicted which are "Hypertension" or "Normal". This is only one embodiment; any number of different classifications would also work. For example, there may be two, three, four or more classes. For example "Low Blood Pressure" could be added.

High blood pressure was tagged in about 20% of the total dataset used, however training may be more effective when using a balanced dataset which is the case here. The validation set is not balanced in this embodiment which reflects the accuracy of the distribution in the real world, but could be balanced in other embodiments. In some embodiments the neural network has an equal chance of being fed an instance of one of the categories. In various embodiments, at least 50% or 75% of the training set includes images balanced among the possible classes.

A large dataset containing over 1.8 million ultrasound images with annotations about the patient's blood pressure status was used for the training and validation of this invention. Optionally, the image size can be set to 400 by 400 pixels. Most of the images in this dataset are several times this size and are reduced in size for training and inference efficiency. Accuracy can increase with increasing image size, however there can be diminishing returns. Alternative embodiments use images of at least 224×224 pixels, 640×640 pixels, or 2048×2048 pixels, or any range therebetween.

This will create an object to feed data to the neural network during training and validation. In this example, 10% of the studies are put into a validation set which is used to monitor training. The validation set contains the same distribution of high blood pressure that exists in the original dataset. The data is balanced for training; however, the validation set is the natural distribution and not balanced in any way. The batch size is arbitrarily set to 48 images but can be adjusted if necessary. Adding the function aug_transforms causes each image to be randomly augmented which can reduce overfitting. Examples of augmentation include but are not limited to adjusting brightness, contrast, and flipping the image horizontally. This embodiment uses Cross Entropy as the loss function and it is training as a label classification problem where there is exactly one label for each image. Other embodiments could use other loss functions such as mean squared error if the data is viewed as a regression problem.

```
from fastai.vision.all import*
# Define data transformations
tfms=aug_transforms( )
image_size=400
# Get image file names from the specified path
fnames=get_image_files(path)
# Create a DataBlock for label classification
dblock=DataBlock(
    blocks=(ImageBlock, CategoryBlock),
    get_items=get_image_files,
    get_y=Pipeline([parent_label]),
    splitter=GrandparentSplitter( ),
    item_tfms=Resize(image_size),
    batch_tfms=[*tfms])
# Create DataLoader
dls=dblock.dataloaders(path, bs=48)
```

Create an object which will control training and inference at a high level. Using a high value for weight decay is one example. Other forms of regularization of the weight values may have similar effects.

Obtain a pretrained network for use in transfer learning, however training a neural network from an initial randomized form will also work. In this case ResNet-152 is used. Other variations of resnet will work and the more layers the better the accuracy. Many other neural networks will also give usable results. The example below illustrates an example of training. The parameters and steps may be varied in alternative embodiments.

Create a learner object with a CNN architecture (however vision transformers may also be used)

```
learn=cnn_learner(dls,
resnet152,
cbs=[ShowGraphCallback( )],
wd=0.1,
metrics=[accuracy],
loss_func=CrossEntropy WithLogitsLossFlat( ))
```

This will freeze the parameters of the convolutional part of the neural network and will allow training of just the linear layers. Other embodiments will not necessarily require the step of freezing layers.

learn.freeze( )

Train the neural network for 10 epochs while gradually increasing then decreasing the learning rate with a scheduler. The maximum learning rate will be 1e-3. Other embodiments may use an alternative training schedule.

learn.fit_one_cycle(10, 1e-3)

This will allow the entire neural network to be trained including the convolutional layers.

learn.unfreeze( )

Further train the neural network for 5 epochs while gradually increasing then decreasing the learning rate with a scheduler. The maximum learning rate will be 1e-5.

learn.fit_one_cycle(5, 1e-5)

Further train the neural network for 5 epochs while gradually increasing then decreasing the learning rate with a scheduler. The maximum learning rate will be 1e-5.

learn.fit_one_cycle(5, 1e-5)

Best validation accuracy of this embodiment is 79%.

This network allows for the identification of the specific anatomical views of the study that are most useful for making this determination. Specific anatomical views or any other information fed to the network can be excluded if it is commonly uninformative, or the various views can be weighted in calculating the final determination.

Each determination outputs a score of how confident the model is which can be used in real time on the ultrasound machine to inform the ultrasound technician when a view which will improve accuracy has been obtained, or the software can automatically capture high confidence views as they are found with no effort from the technician required. This technique can be used to create training sets for continuous improvements in updated models which is a feedback loop for capturing better data for training future models.

The trained system is optionally used to provide an ultrasound technician with real-time feedback. For example, the system may inform the technician when images expected to be the most predictive have or have not been obtained. The system can request that the technician obtain images of specific anatomy of the patient. When an obtained image is identified as being determinative of high blood pressure, the system may request that the technician obtain additional images to confirm or negate the determination of high blood pressure. For example, if an image of one part of the anatomy (e.g., a heart) determines high blood pressure the system may request that the technician obtain further images of that anatomy or further images of another part of the patient's anatomy (e.g., lungs).

Making determinations based on individual ultrasounds and then aggregating these individual determinations can be useful in itself, but the method can also be improved upon. One concern with this method is that within a single ultrasound recording session some ultrasound images may show a confident high blood pressure while ultrasound images of another part of the anatomy will confidently determine normal blood pressure, making a simple aggregation less effective. Accordingly, neural networks have been created that allow multiple images to be classified in a single pass through a neural network or sequence of networks. As the number of images simultaneously fed into a neural network increases, the accuracy also typically increases. Therefore, more efficient methods of passing (in parallel, or sequentially) multiple images through a single network (or sequence of networks) were developed.

This does not necessarily have to be a classification problem. The values to determine could be numeric values representing the desired target and a neural network to perform a regression is created instead.

Training data can be created by training a neural network to modify images from one class into another if the data is limited for a particular class. An example of a neural network which can convert images from one class to another is a cyclegan.

It is not necessary for images to be used. The underlying sound waves captured by the ultrasound machine before conversion into an image could also be used as an alternative to or in addition to images for this determination.

Transformer Aggregation Architecture

A neural network can be created which can extract the useful information from each image which is then aggregated using multiple neural networks combined into a single neural network using a transformer style architecture, however these networks could be separate in other embodiments. An ultrasound session is one in which a technician takes a set of images in one interaction with a patient. Considering many ultrasound sessions exceed 100 images this is useful for processing efficiency and accuracy. Transformers can be applied to sequential (or time series) data where data points are correlated in a sequence. The ultrasound images in an ultrasound session don't have a significant amount of order to them, if any, however this type of network can carry information from a previous step of processing a single image forward and this combined information can be classified after each image in an ultrasound session is processed. Ultrasound sessions do not have a significant amount of order because an ultrasound technician typically jumps from viewing one anatomical feature to another anatomical feature. It is possible to record a video of the entire session and in these embodiments the images in the video have a sequential nature and this general technique can be employed.

```
from fastai.vision.all import*
from pathlib import Path
```

Get the data which is divided into training, validation, and test sets. The training data is created in an unusual way. Instead of just using each study as a separate folder of images, folders are created which randomly sample a range of images from pools of all high blood pressure and normal blood pressure studies. It is also possible to sample images from a pool of each class of the desired sequence length at run time. Other embodiments use 2, 3 or more classes or numeric values. There is at least one reason to do this.

Some patients may not have a stable or accurate blood pressure reading, which means the training data can contain a significant number of mislabeled studies. By taking a random selection it makes it possible for each training sample to have some ultrasounds which contain the needed information to make a correct determination.

It should also be noted that multiple ultrasound sessions are commonly performed on a single patient. Multiple sessions from a single patient could also be combined when performing a determination of high blood pressure across the entire time span.

A single session may indicate high blood pressure but may not have a high confidence. Therefore, the system may indicate that a follow up session is desired and potentially when the follow up session should be conducted.

Data Acquisition

To obtain the paths to folders containing images from individual studies, the following function can be used:

```
def get_sequence_paths(path):
    sequence_paths=[ ]
    for folder in path.ls( ):
        for c in folder.ls( ):
            sequence_paths+=c.ls( )
    return sequence_paths
folders=get_sequence_paths(IMAGES_PATH)
```

In this example, the sequence length is set to 36 images, but a smaller or larger range can be used. More images may improve results, but there can be diminishing returns. The image size used here is 400×400 pixels, which is larger than the typical 224×224 pixels used in image classification problems. However, smaller or larger images can also be utilized:

```
seq_len=36
image_size=400
```

A custom ImageTuple class is defined to handle image sequences and display them:

```
class ImageTuple(Tuple):
    def show(self, ctx=None, **kwargs):
        n=len(self)
        img0, img1, img2=self[0], self[n//2], self[n-2]
        if not isinstance(img1, Tensor):
            t0, t1, t2=tensor(img0), tensor(img1), tensor(img2)
            t0, t1, t2=t0.permute(2, 0, 1), t1.permute(2, 0, 1), t2.permute(2, 0, 1)
        else:
            t0, t1, t2=img0, img1, img2
        return show_image(torch.cat([t0, t1, t2], dim=2), ctx=ctx, **kwargs)
```

An ImageTupleTransform is also created to encode images into tuples for our dataset:

```
class Image Tuple Transform(Transform):
    def_init_(self, seq_len=36):
        self.seq_len=seq_len
    def encodes(self, path):
        images=path.ls( )
        return Image Tuple(tuple(PILImage.create(f) for f in
            L(random.choices(list(images),
    k=self.seq_len)) if os.path.isfile(f)))
tfms=aug_transforms(flip_vert=False)
grandparent_splitter=GrandparentSplitter( )files)
itfm=Image Tuple Transform(seq_len=seq_len)
ds=Datasets(files, tfms=[[itfm], [parent_label, Categorize]], splits=grandparent_splitter)
dls=ds.dataloaders(bs=bs,        after_item=[Resize(image_size), ToTensor], after_batch=[*tfms, IntToFloatTensor], drop_last=True)
```

Encoder Class

The Encoder class loads a model pretrained on single ultrasound images, removes the final classification layer, and returns 512 features for each image:

```
class Encoder(Module):
    def_init_(self, **kwargs):
        model=load_learner("davit_large").model
        self.body=model[0]
        self.head=model[1][:−4]
    def forward(self, x):
        return self.head(self.body(x))
```

This class allows features to be extracted from images using a pretrained model. The number of features can be adjusted as needed for specific use cases.

The following module takes the features from each image and classifies the entire sequence of images.

```
import torch
import torch.nn as nn
import torch.nn.functional as F
class TransformerEncoder(Module):
    def __init__(self, num_classes=2, d_model=512, nhead=8, num_encoder_layers=6,
dim_feedforward=2048, dropout=0.1):
        self.transformer_encoder = nn.TransformerEncoder(
            nn.TransformerEncoderLayer(d_model, nhead, dim_feedforward, dropout),
            num_encoder_layers
        )
        self.fc = nn.Sequential(
            nn.Linear(d_model, num_classes),
        )
    def forward(self, x):
        x = self.transformer_encoder(x)
        x = x.mean(dim=1) # Pooling operation, you can replace this with another method if needed
        x = self.fc(x)
        return x
Example usage:
dls_c = 2
model = TransformerEncoder(num_classes=dls_c, d_model=512, nhead=8,
num_encoder_layers=6, dim_feedforward=2048, dropout=0.1)
```

Create a Learner object which will control training and inference at a high level. Using a high value for weight decay is helpful in making a correct determination.

GradientAccumulation can be used if GPU memory constraints require it. This will accumulate gradients for 32 items before making an update to the weights of the network.

```
import torch.nn as nn
from fastai.learner import cnn_learner, Learner
from fastai.vision.all import ShowGraphCallback, GradientAccumulation, SaveModelCallback
class TransformerModel(nn.Module):
    def __init__(self, num_classes, d_model=512, nhead=8, num_encoder_layers=6,
dim_feedforward=2048, dropout=0.1):
        # transformer architecture here   def forward(self, x):
        # Forward pass through the transformer# Custom splitter function to separate transformer
encoder from other layers
def transformer_splitter(model):
    transformer_layers = [ ]
    other_layers = [ ]
    for name, param in model.named_parameters( ):
        if 'transformer_encoder' in name:
            transformer_layers.append(param)
        else:
            other_layers.append(param)
    return [transformer_layers, other_layers]
# Create your data loaders (dls) here
# Replace 'dls' with the actual data loaders
# Instantiate your TransformerModel
model = TransformerModel(num_classes=dls.c)
# Create a Learner with the model and custom splitter
learn = Learner(dls,
        model,
        wd=0.3,
        metrics=[accuracy],
        cbs=[ShowGraphCallback( ), GradientAccumulation( ),
SaveModelCallback(monitor='valid_loss', fname='Transformer_Model')],
        splitter=transformer_splitter).to_fp16( )
```

Train the neural network for 5 epochs while gradually increasing then decreasing the learning rate with a scheduler. The maximum learning rate will be 1e−3. These parameters are simply chosen for this embodiment, many other choices would also work.

learn. freeze( ) learn.fit_one_cycle(5, 1e−3)

Alternative Embodiments

To aggregate the individual determinations for a study run each through a tournament to determine final classification.

Reinforcement learning can be used in place of the transformer shown.

Use multiple models trained on different subsets of the data to create ensembles which typically increases accuracy.

Use additional data about the patient in combination with the images such as age or relevant events in the medical history of a patient.

Additional outputs in addition to the lab or clinical values can be used. Some examples are age, BMI, sex, among others. Having multiple outputs for determination can improve the overall accuracy of the determination due to the inherent relationships between the various items being determined. Any of these alternative determinations can be performed without the clinical or lab values if desired.

The systems and methods disclosed herein have been applied to real world data obtained from a clinical context and have been shown to consistently produce a positive predictive value above 91% and a negative predictive value above 75%.

Several embodiments are specifically illustrated and/or described herein. However, it will be appreciated that modifications and variations are covered by the above teachings and within the scope of the appended claims without departing from the spirit and intended scope thereof. For example, while ultrasound images and clinical or lab value determination are taught herein by way of example, the systems and methods described herein may be applied to other medical information and conditions. Examples, include determination of physical activity capability, physical or mental stress, sunlight exposure, diet, nutritional deficiencies, sleep deprivation, radiation exposure, and/or any other clinical or lab value the precursors of which may be present in an ultrasound image. The methods and systems disclosed may be used to determine a current clinical state separately or in combination with the (optionally quantitative or qualitative) determination of a future state. The systems and methods disclosed herein may also be used to predict future clinical or lab values of a patient. For example, development of cancer markers, heart problem indicators, poor function of various organs indicators, and/or the like. It will be understood that the terms "predict" and "determine" are used interchangeably herein.

While the teachings herein include use of medical images, e.g., ultrasound images, in various embodiments, the systems and methods may use raw data other than in the form of images. For example, Image Analysis Logic 130 is optionally trained to process raw ultrasound data rather than or in addition to images generated from such data.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

The "logic" discussed herein is explicitly defined to include hardware, firmware or software stored on a non-transient computer readable medium, or any combinations thereof. This logic may be implemented in an electronic and/or digital device to produce a special purpose computing system. Any of the systems discussed herein optionally include a microprocessor, including electronic and/or optical circuits, configured to execute any combination of the logic discussed herein. The methods discussed herein optionally include execution of the logic by said microprocessor.

Computing systems and/or logic referred to herein can comprise an integrated circuit, a microprocessor, a personal computer, a server, a distributed computing system, a communication device, a network device, or the like, and various combinations of the same. A computing system or logic may also comprise volatile and/or non-volatile memory such as random-access memory (RAM), dynamic random access memory (DRAM), static random access memory (SRAM), magnetic media, optical media, nano-media, a hard drive, a compact disk, a digital versatile disc (DVD), optical circuits, and/or other devices configured for storing analog or digital information, such as in a database. A computer-readable medium, as used herein, expressly excludes paper. Computer-implemented steps of the methods noted herein can comprise a set of instructions stored on a computer readable medium that when executed cause the computing system to perform the steps. A computing system programmed to perform particular functions pursuant to instructions from program software is a special purpose computing system for performing those particular functions. Data that is manipulated by a special purpose computing system while performing those particular functions is at least electronically saved in buffers of the computing system, physically changing the special purpose computing system from one state to the next with each change to the stored data.

What is claimed is:

1. A system configured to make a medical determination, the system comprising:
    an image storage configured to store non-invasive images of a body part of a patient,
    the non-invasive images previously acquired via process that does not require cutting or puncturing the patient's skin;
    image analysis logic comprising a trained neural network in communication with the image storage and configured to provide a determination regarding a clinical or lab value of the patient, the determination based on the stored non-invasive images and additionally based on a clinical data set;
    a user interface configured to provide the determination to a user; and
    a processor configured to execute at least the image analysis logic.

2. The system of claim 1 wherein the image analysis logic includes first logic configured to analyze the stored non-invasive images to determine a present clinical or lab value at the time the stored images were acquired.

3. The system of claim 1 wherein the image analysis logic includes second logic configured to determine a future clinical or lab value within a timeframe.

4. The system of claim 1 wherein the image analysis logic is configured to employ a regression algorithm to provide the determination as a range.

5. The system of claim 1 wherein the image analysis logic is configured to employ a classification algorithm to provide the determination as one of a plurality of categories.

6. The system of claim 1 wherein the image analysis logic is further configured to provide the determination based additionally on a clinical data set.

7. The system of claim 1 further comprising an image generator configured to acquire images, some of the images becoming the stored non-invasive images.

8. The system of claim 7 further comprising feedback logic configured to provide guidance to a user of the image generator in acquiring the stored non-invasive images.

9. The method of claim 8 wherein the feedback logic further processes the determination based on the stored non-invasive images and the clinical data set, as provided by the trained neural network, to provide the guidance to the user to acquire additional non-invasive images.

10. The method of claim 8 wherein the guidance depends on a quality of the determination based on the stored non-invasive images and the clinical data set.

11. The method of claim 8 wherein the guidance comprises instructing the user to obtain non-invasive images of specific portions of the patient's anatomy.

12. The system of claim 3 wherein the second logic is configured to determine the future clinical or future lab value that depends on a probability that the medical determination will occur within a future timeframe based on analysis of the stored non-invasive images.

13. The method of claim 1 wherein the guidance depends on a quality of the quantitative determination and/or a classification of non-invasive images already acquired.

14. The method of claim 1 wherein the guidance informs the user that additional non-invasive images can be expected to improve accuracy of the determination regarding a clinical or lab value of the patient.

15. A method for training a neural network to make a medical determination, the method comprising:
- receiving a set of non-invasive images of body parts of a plurality of patients, the non-invasive images tagged with information concerning the current or future lab values, the non-invasive images having been previously generated without puncturing or cutting the patient's skin;
- dividing the set of non-invasive images into a training set and a validation set;
- providing the images of the training set, and their tags, to a neural network to train the neural network to determine a current or future, lab or clinical, quantitative values based on the non-invasive images of the body parts; and
- providing images of a single patient from the validation set to the neural network to make the medical determination, and comparing the medical determination to the tag associated with the non-invasive images.

16. The method of claim 15 wherein the non-invasive images are ultrasound images.

17. The method of claim 15 further comprising classifying the non-invasive images before providing the images of the training set to the neural network.

18. The method of claim 15 further comprising resizing the non-invasive images before providing the images of the training set to the neural network.

19. The method of claim 15 wherein the neural network is configured to determine future clinical quantitative values that includes a probability that the medical determination will occur within a future time range as based on analysis of the non-invasive medical images.

20. A method for making a medical determination, the method comprising:
- obtaining a non-invasive image of a body part of a patient, the non-invasive image acquired without puncturing or cutting the patient's skin;
- providing the non-invasive image to a neural network that has been trained to determine the patient's current or future clinical or lab quantitative values from the image of the body part; and
- receiving the determination of the clinical or lab value.

21. The method of claim 20 wherein the non-invasive image is an ultrasound image.

22. The method of claim 20 wherein the neural network employs a regression algorithm and receiving the determination includes receiving a range.

23. The method of claim 20 wherein the neural network employs a classification algorithm and receiving the determination includes receiving one of a plurality of categories.

24. A system configured to make a medical determination, the system comprising:
- an image storage configured to store non-invasive images of a body part of a patient, the non-invasive image acquired without puncturing or cutting the patient's skin;
- image analysis logic comprising a trained neural network in communication with the image storage and configured to provide a probability that a future clinical or future lab value of the patient will occur within a future time frame, the determination based on the stored non-invasive images and additionally based on a clinical data set;
- a user interface configured to provide the determination to a user; and
- one or more processors configured to execute at least the image analysis logic.

25. A method for training a neural network to make a medical determination, the method comprising:
- receiving a set of non-invasive images of body parts of a plurality of patients, the non-invasive images, the non-invasive image acquired without puncturing or cutting the patient's skin, and the non-invasive images tagged with information concerning future lab values;
- dividing the set of non-invasive images into a training set and a validation set;
- providing the images of the training set, and their tags, to a neural network to train the neural network to determine a probability that a future lab or clinical quantitative values will occur within a future time frame based on the non-invasive images of the body parts; and
- providing non-invasive images of a single patient from the validation set to the neural network to make the medical determination, and comparing the medical determination to the tag associated with the non-invasive images.

* * * * *